United States Patent
Kyou (10) Patent No.: US 11,249,445 B2
(45) Date of Patent: Feb. 15, 2022

(54) ELECTRONIC DEVICE, DISPLAY-UNIT SETTING METHOD AND RECORDING MEDIUM

(71) Applicant: CASIO COMPUTER CO., LTD., Tokyo (JP)

(72) Inventor: Kazuho Kyou, Tachikawa (JP)

(73) Assignee: CASIO COMPUTER CO., LTD., Tokyo (JP)

(*) Notice: Subject to any disclaimer, the term of this patent is extended or adjusted under 35 U.S.C. 154(b) by 259 days.

(21) Appl. No.: 16/356,195

(22) Filed: Mar. 18, 2019

(65) Prior Publication Data

US 2019/0286067 A1    Sep. 19, 2019

(30) Foreign Application Priority Data

Mar. 19, 2018  (JP) .............................. JP2018-050956

(51) Int. Cl.
| | |
|---|---|
| *G06F 3/048* | (2013.01) |
| *G04G 9/00* | (2006.01) |
| *G04G 21/02* | (2010.01) |
| *G06F 3/0484* | (2022.01) |
| *G04R 20/26* | (2013.01) |

(Continued)

(52) U.S. Cl.
CPC ............. *G04G 9/007* (2013.01); *G04G 21/02* (2013.01); *G04R 20/26* (2013.01); *G06F 3/04847* (2013.01); *A61B 5/1112* (2013.01); *A61B 5/681* (2013.01); *A61B 2560/0242* (2013.01)

(58) Field of Classification Search
CPC ........ G04G 9/007; G04G 21/02; G04R 20/26; G06F 3/04847; G06F 9/454; A61B 5/681; A61B 2560/0242; A61B 5/1112
See application file for complete search history.

(56) References Cited

U.S. PATENT DOCUMENTS

| | | | | |
|---|---|---|---|---|
| 2,008,001 A | * | 7/1935 | Burnham | ............... B65D 43/20 |
| | | | | 206/536 |
| 6,085,098 A | * | 7/2000 | Moon | ................... G06F 1/1698 |
| | | | | 455/457 |
| 2008/0016445 A1 | | 1/2008 | Dykes et al. | |

(Continued)

FOREIGN PATENT DOCUMENTS

| | | |
|---|---|---|
| EP | 3 051 407 A1 | 8/2016 |
| JP | H4-075992 U | 7/1992 |

(Continued)

OTHER PUBLICATIONS

Mobvoi, https://forum.mobvoi.com/viewtopic.php?t=2569, Jan. 12, 2018 (Year: 2018).*

(Continued)

*Primary Examiner* — Mohamed Abou El Seoud
(74) *Attorney, Agent, or Firm* — Scully Scott Murphy & Presser (57) ABSTRACT

An electronic device is communicatively connected to an electronic terminal configured to display an output value of a sensor. The electronic device includes a storage unit and a processor. The storage unit is stores a first city to be set in the electronic terminal. The processor fixes or changes a display-unit of the output value of the sensor to be displayed on the electronic terminal, based on the first city and a display language set in an OS of the electronic device.

11 Claims, 7 Drawing Sheets

(51) Int. Cl.
    *A61B 5/00*           (2006.01)
    *A61B 5/11*           (2006.01)

(56) References Cited

U.S. PATENT DOCUMENTS

| | | |
|---|---|---|
| 2014/0176426 A1 | 6/2014 | Morohoshi |
| 2015/0058047 A1* | 2/2015 | Turk ................. G06Q 10/04 705/4 |
| 2017/0176952 A1* | 6/2017 | Misaki ................. G04G 9/0076 |

FOREIGN PATENT DOCUMENTS

| | | |
|---|---|---|
| JP | H07-333365 A | 12/1995 |
| JP | 2001-324355 A | 11/2001 |
| JP | 2002-116219 A | 4/2002 |
| JP | 2004-251887 A | 9/2004 |

OTHER PUBLICATIONS

Extended European Search Report dated Jul. 18, 2019 received in European Patent Application No. EP 19163827.9.
Ticwatch S—cannot find where to change from celsius to farenheit, Moderators, https://form.mobvoi.com/viewtopic.php?t=2569, pp. 1-3, Jan. 12, 2018, May 27, 2021.
First Office Action dated Nov. 23, 2021 received in Chinese Patent Application No. CN 201910202821.6 together with an English language translation.

* cited by examiner

| offset | Fields | Additional Information | | |
|---|---|---|---|---|
| | | bit | size | Definition |
| 0 | ALTITUDE SETTING | 0 | 1 | 0:Meter |
| | | | | 1:Feet |
| 1 | ATMOSPHERIC PRESSURE SETTING | 0 | 1 | 0:hectpascal (hPa) |
| | | | | 1:Inches of mercury (inHg) |
| 2 | TEMPERATURE SETTING | 0 | 1 | 0:degree Celsius |
| | | | | 1:fahrenheit |
| 3 | GPS SETTING | 0 | 1 | 0:Kilometer |
| | | | | 1:Mile |
| 4 | UNIT FIXING | 0 | 1 | 0:Unit fixing is not necessary (HT). |
| | | | | 1:Unit fixing is necessary (HT). |
| | | 1 | 1 | 0:Unit fixing is not necessary (WT). |
| | | | | 1:Unit fixing is necessary (WT). |

ELECTRONIC DEVICE, DISPLAY-UNIT SETTING METHOD AND RECORDING MEDIUM

CROSS-REFERENCE TO RELATED APPLICATIONS

This application is based on and claims priority under 35 USC 119 from Japanese Patent Application No. 2018-050956 filed on Mar. 19, 2018, the contents of which are incorporated herein by reference.

TECHNICAL FIELD

The present disclosure relates to an electronic device, a display-unit setting method and a recording medium.

DESCRIPTION OF THE RELATED ART

A digital wrist watch having therein sensors configured to detect a temperature and a pressure and configured to display a temperature, an altitude, and a wind speed has been disclosed (refer to JP-A-1-107-333365). In the wrist watch, display-units of the sensors are "°C.", "m/sec", "m" and "ft/sec".

In many cases, a watch is set and information of the watch is checked using an electronic device (for example, a smart phone) capable of performing near field communication. At this time, display-units of the electronic device pairing with the watch disclosed in JP-A-H07-333365 are also "°C.", "m/sec", "m" and "ft/sec".

In Japan, Celsius of "°C." and the metric system of "m", "m/s" and the like are standards. However, in foreign countries such as USA and the United Kingdom, Fahrenheit and the yard-pound system of "Feet", "yard", "pound" and the like are used, in many cases. A Japanese who resides in Japan may fix the display-units with Celsius and the metric system. On the other hand, when a foreigner who resides in Japan and when the foreigner uses a watch in which Japan is set as a hometown, a troublesome may be caused if the display-units are fixed with Celsius and the metric system. That is, for the foreigner who resides in Japan, it is preferably to set the display-units not only with Celsius and the metric system but also with Fahrenheit and the yard-pound system.

SUMMARY

According to a preferred embodiment, an electronic device is communicatively connected to an electronic terminal configured to display an output value of a sensor. The electronic device includes a storage unit and a processor. The storage unit stores a first city to be set in the electronic terminal. The processor fixes or changes a display-unit of the output value of the sensor to be displayed on the electronic terminal, based on the first city and a display language set in an OS of the electronic device. In the following description, the reference numerals and characters in parentheses are exemplary.

A display language that is to be displayed on a display unit of the electronic device is set in the OS with Japanese for a Japanese, while the display language is set in the OS with English for an American. For example, when the display language is set with Japanese, the display-unit setting unit fixes the display-units with Celsius and the metric system, and when the display language is set with English, the display-unit setting unit enables units of Fahrenheit and the yard pound system to be selected and displayed.

DETAILED DESCRIPTION OF THE PREFERRED EMBODIMENTS

Hereinafter, embodiments will be described in detail with reference to the drawings. The respective drawings just show schematically the embodiments so as to fully understand the embodiment. Also, in the respective drawings, the common constitutional elements and the similar constitutional elements are denoted with the same reference numerals, and the overlapping descriptions thereof are omitted.

First Embodiment

Figure 1:
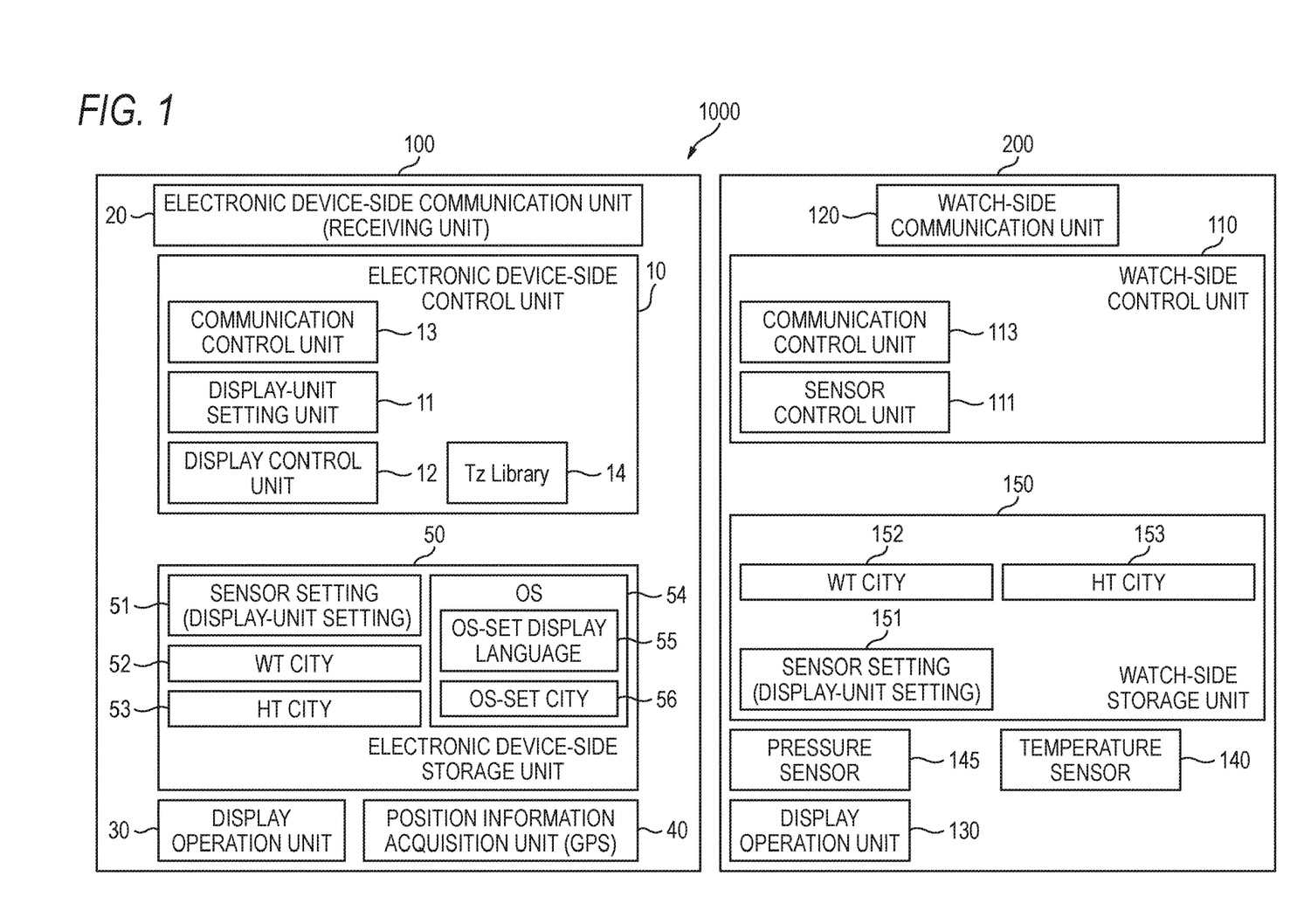
FIG. 1 is a configuration view of a measurement system that is used for an electronic device of an embodiment.
Figure 2:
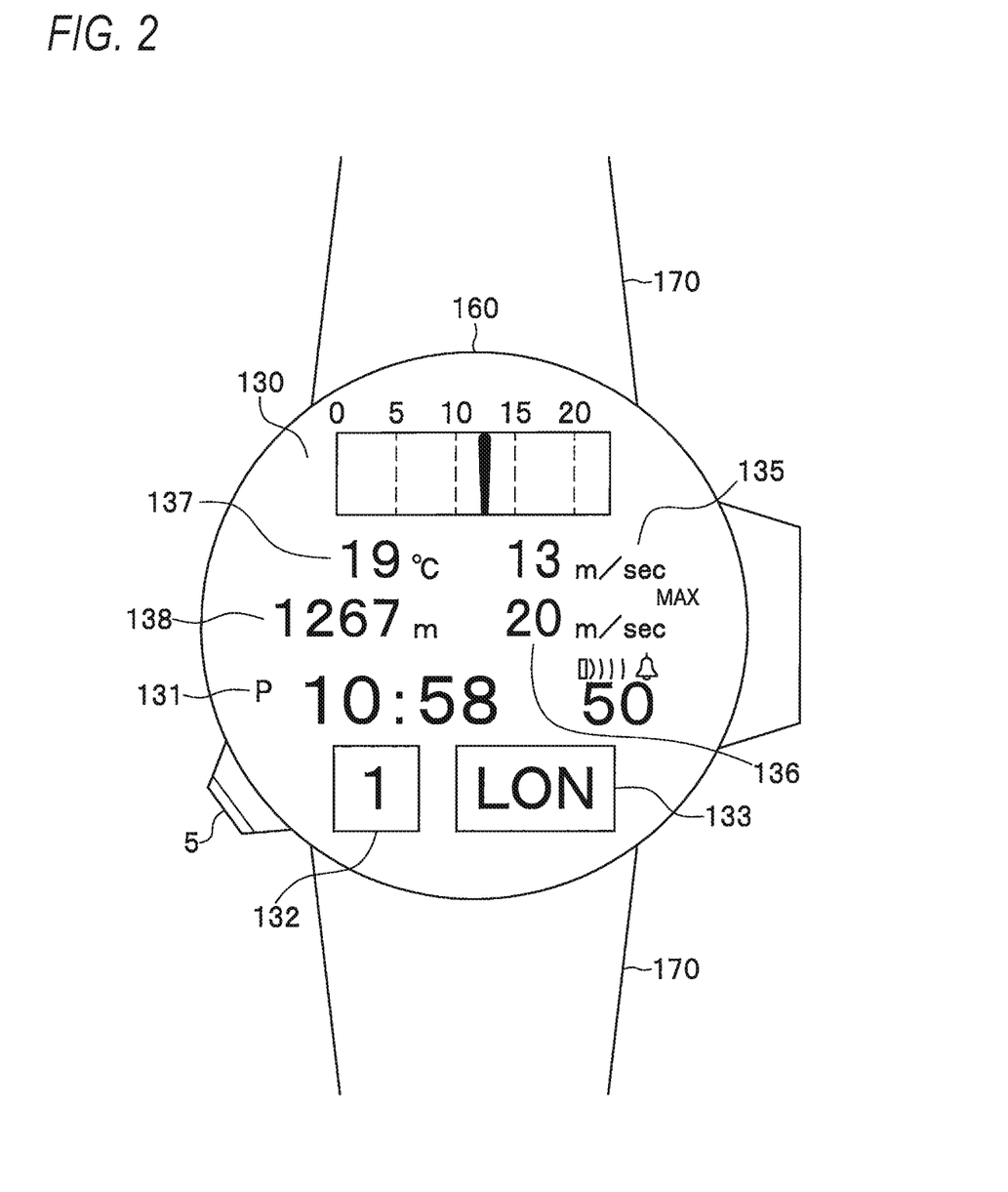
FIG. 2 depicts an outer shape of a watch configured to operate in conjunction with the electronic device of the embodiment.

FIG. 1 is a configuration view of a measurement system that is used for an electronic device of an embodiment, and FIG. 2 depicts an outer shape of a watch configured to operate in conjunction with the electronic device of the embodiment.

In a measurement system 1000, an electronic device 100 and a watch 200 are communicatively connected to each other. The electronic device 100 is, for example, a smart phone, and includes an electronic device-side control unit 10, an electronic device-side communication unit 20 (an electronic terminal unit setting unit) as a receiving unit, an electronic device-side storage unit 50, a display operation unit 30, and a position information acquisition unit 40.

The watch 200 is a measurement device including a watch-side control unit 110, a watch-side communication unit 120, a watch-side storage unit 150, a display operation unit 130, a temperature sensor 140, and a pressure sensor 145, too. The watch-side control unit 110 is a CPU (Central Processing Unit), and is configured to implement functions of a sensor control unit 111 and a communication control unit 113 by executing a program. The watch-side storage unit 150 has storage areas of a sensor setting 151, a world time city 152, and a home time city 153.

As shown in FIG. 2, the watch 200 includes a case 160 having the display operation unit 130 and an operation switch 5, and a band 170. The display operation unit 130 includes a time display area 131, a world time display area 132, a world time city display area 133, a wind speed value display area 135, a maximum wind speed value display area 136, a temperature display area 137, and an altitude display area 138.

The time display area 131 displays time of a hometown, for example, 10:58:50 in Japan. The world time display area 132 is an area in which time of a world time, for example, "1" o'clock in London is displayed. In the world time city display area 133, a world time city, for example, a symbol "LON" indicative of London is displayed.

The wind speed value display area 135 is an area in which a wind speed is displayed using the pressure sensor 145, and for example, "13 m/sec" is displayed. The maximum wind speed value display area 136 is an area in which a maximum value of the wind speed in predetermined time is displayed, and for example, "20 m/sec MAX" is displayed. The temperature display area 137 is an area in which a temperature measured using the temperature sensor 140 is displayed, and for example, "19° C." Celsius is displayed.

The wind speed V [m/sec] is calculated based on a Bernoulli's theorem with respect to a difference between an output value of the pressure sensor 145 at a calm state and an output value of the pressure sensor 145 at a wind pressure-applied state. That is, $$V=\{2\cdot(Pt-Ps)/\rho\}1/2$$

here, (Pt−Ps) is a pressure difference, and ρ is an air density and is a value temperature compensated with an atmospheric temperature upon measurement.

The altitude display area 138 is an area in which an altitude is displayed using the temperature sensor 140 and the pressure sensor 145, and for example, "1267 m" is displayed. Here, the altitude h[m] at the atmospheric pressure P [hPa] and the atmospheric temperature T [° C.] can be calculated by a following equation, for example. Here, a sea-level atmospheric pressure Po is 1013.25 [hPa].

$$h=[\{(Po/P)1/5.257-1\}\times(T+273.15)]/0.0065$$

Returning to FIG. 1, the electronic device-side communication unit 20 is configured to perform near field communication with the watch 200, through Bluetooth (registered trademark), for example. The display operation unit 30 is an LCD (Liquid Crystal Display) panel having a touch panel function. The position information acquisition unit 40 is a GPS (Global Positioning System), and is configured to output a current positon by latitude/longitude.

The electronic device-side control unit 10 is a CPU, and is configured to implement functions of a display-unit setting unit 11, a display control unit 12, a communication control unit 13, and a Tz_Library 14 by executing an OS and an application program. The display-unit setting unit 11 is configured to set units to be displayed on the display operation unit, based on a display language (OS language) set in the OS. For example, when the OS language is Japanese, the display-unit setting unit 11 fixes the display-units by Celsius of "°C." and the metric system such as "m" and "m/s". On the other hand, when the OS language is English, the display-unit setting unit 11 sets that the display-units may be any one of Celsius of "°C." and the metric system such as "m" and "m/s" or Fahrenheit of "T" and the yard-pound system such as "Feet", "yard", "pound" and the like.

The display control unit 12 is configured to generate image data of a display screen that is to be displayed on the display operation unit 30. The display screen includes a setting button with which a home time city and a world time city are set at the electronic device 100-side, a change button with which the home time city and the world time city are switched at the electronic device 100-side, a sensor setting screen, and the like.

Figure 3:
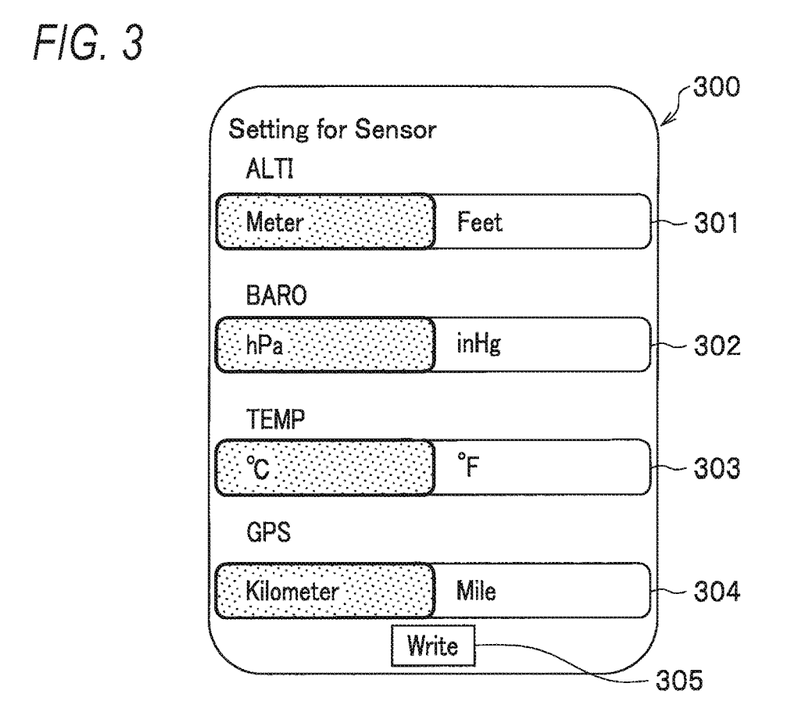
FIG. 3 depicts an example of an English sensor setting screen that is to be displayed by the electronic device of the embodiment.
Figure 4:
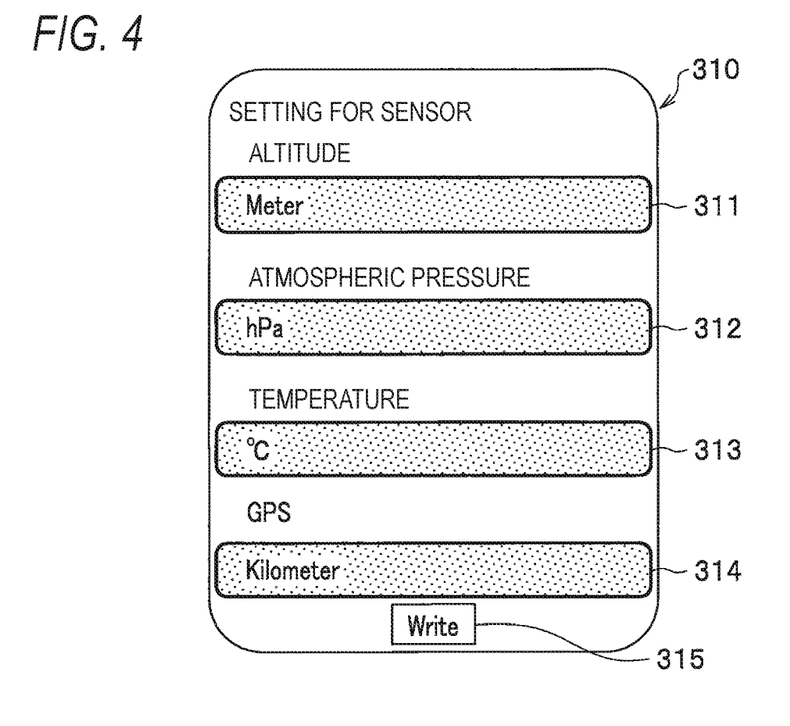
FIG. 4 depicts an example of a Japanese sensor setting screen that is to be displayed by the electronic device of the embodiment.

FIG. 3 depicts an example of an English sensor setting screen that is to be displayed by the electronic device of the embodiment, and FIG. 4 depicts an example of a Japanese sensor setting screen that is to be displayed by the electronic device of the embodiment.

An English sensor setting screen 300 (FIG. 3) is displayed with English and is a screen that may be displayed not only when an owner is an American or a British person but also when a Japanese resides in a foreign country. The English sensor setting screen 300 has a character string "Setting for Sensor" displayed at the uppermost part, and includes an altitude unit setting bar 301, an atmospheric pressure unit setting bar 302, a temperature unit setting bar 303, a GPS distance unit setting bar 304, and a "Write" button 305.

The altitude unit setting bar 301 is to select the display-unit to any one of "Meter" and "Feet", and here, "Meter" is set. The atmospheric pressure unit setting bar 302 is to select the display-unit to any one of "hPa" and "inHg", and here, "hPa" is set. The temperature unit setting bar 303 is to select the display-unit to any one of Celsius and Fahrenheit, and here, Celsius "°C." is set. The GPS distance unit setting bar 304 is to select the display-unit to any one of "Kilometer" and "Mile", and here, "Kilometer" is set. When the "Write" button 305 is pushed, the selected unit setting is registered in a sensor setting 51 of the electronic device-side storage unit 50 and is transmitted to the watch 200. That is, when the "Write" button 305 is pushed, the display-units of the watch 200 are set.

A Japanese sensor setting screen 310 (FIG. 4) is displayed with Japanese, and is a screen that is displayed when a Japanese owner resides in Japan or in a foreign country. The Japanese sensor setting screen 310 has a character string "Setting for Sensor" displayed at the uppermost part, and includes an altitude unit setting bar 311, an atmospheric pressure unit setting bar 312, a temperature unit setting bar 313, a GPS distance unit setting bar 314, and a "Write" button 305.

The altitude unit setting bar 311 indicates a state where the display-unit is fixed to "Meter". The atmospheric pressure unit setting bar 312 indicates a state where the display-unit is fixed to "hPa". The temperature unit setting bar 313 indicates a state where the display-unit is fixed to "°C.". The GPS distance unit setting bar 314 indicates a state where the display-unit is fixed to "Kilometer". When the "Write" button 315 is pushed, the selected unit setting is registered in the sensor setting 51 of the electronic device-side storage unit 50 and is transmitted to the watch 200.

Returning to FIG. 1, the communication control unit 13 is a driver configured to control the electronic device-side communication unit 20. The Tz_Library 14 specifies a region based on position information (latitude/longitude) acquired by the position information acquisition unit 40.

The electronic device-side storage unit 50 has regions for storing information about a world time city 52, a home time city 53, and the sensor setting 51, and has regions for storing information about an OS-set display language 55 and an OS-set city 56 in an OS 54. The information about the world time city 52, the home time city 53 and the sensor setting 51 is set by receiving the information about the world time city 152, the home time city 153 and the sensor setting 151 from the watch 200, via the electronic device-side communication unit 20.

On the other hand, the information about the world time city 52, the home time city 53 and the sensor setting 51 is transmitted to the watch 200 and is set in the world time city 152, the home time city 153 and the sensor setting 151. That is, the electronic device-side communication unit 20 has a function as a watch unit setting unit to set a display-unit of the watch 200.

The world time city 52 is an area in which a city name to be selected from worldwide cities is stored, and a stay city at which an owner temporarily resides is selected, for example. In the home time city 53, a country or city (for example, Japan or Tokyo) in which an owner resides is stored.

Figure 5:
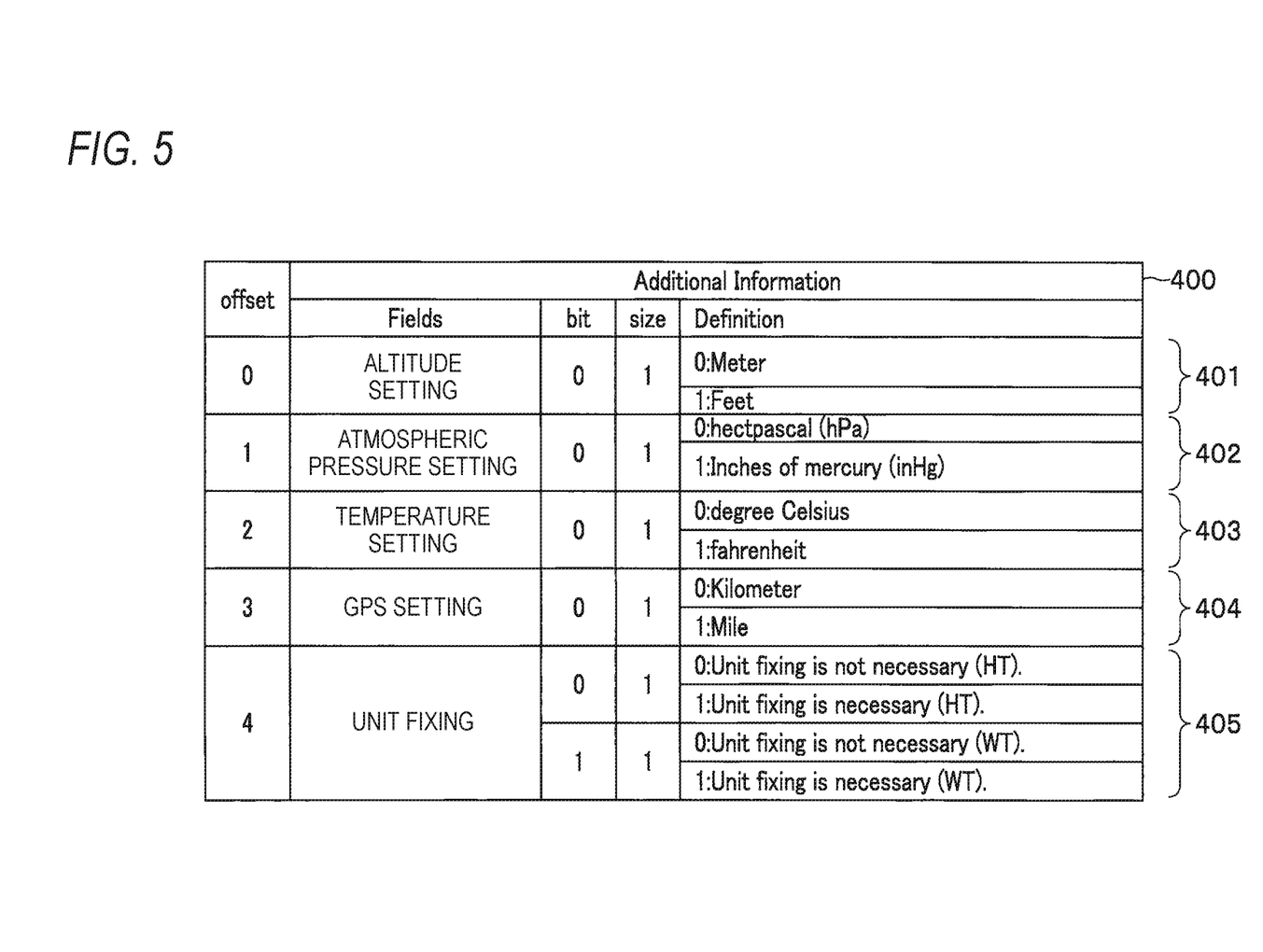
FIG. 5 depicts an example of a data format to set display-units.

FIG. 5 depicts an example of a data format to set the display-units.

A data format 400 is a data format of the sensor setting 151, and includes fields of an altitude setting 401, an atmospheric pressure setting 402, a temperature setting 403, a GPS data setting 404, and a unit fixing setting 405. Each field is defined such that a display-unit of a sensor is set by setting any one of bit 0 and bit 1 of offsets 0 to 4, to "0" or "1".

The altitude setting 401 is to set the display-unit of the altitude to any one of "Meter" and "Feet". For example, when bit 0 of offset 0 is set to "0", "Meter" is set. Also, when bit 0 of offset 0 is set to "1", "Feet" is set. The atmospheric pressure setting 402 is to set the display-unit of the atmospheric pressure to any one of "hPa" (hectopascal) and "inHg" (inches of mercury). For example, when bit 0 of offset 1 is set to "0", "hPa" is set. Also, when bit 0 of offset 1 is set to "1", "inHg" is set.

The temperature setting 403 is to set the display-unit of the temperature to any one of Celsius and Fahrenheit. For example, when bit 0 of offset 2 is set to "0", Celsius is set. Also, when bit 0 of offset 2 is set to "1", Fahrenheit is set. The GPS data setting 404 is to set the display-unit of the distance to any one of "km" (Kilometer) and "Mile". When bit 0 of offset 3 is set to "0", "km" is set. Also, when bit 0 of offset 3 is set to "1", "Mile" is set.

The unit fixing setting 405 is to set whether it is necessary to fix a unit to a unit that is used in the home time city or any unit can be used, and whether it is necessary to fix a unit to a unit that is used in the world time city or any unit can be used.

For example, when the hometown is "Japan", it is necessary to fix the units by Celsius and the metric system such as "in" and "m/s". At this time, bit 0 of offset 4 is set to "1". Also, when the hometown is "United Kingdom", any units of Celsius and the metric system such as "m" and "m/s" or Fahrenheit and the yard-pound system such as "Feet", "pound" and "yard" may be used. At this time, bit 0 of offset 4 is set to "0".

Also, a British person who resides in Japan may set the world time city to "Japan". At this time, when the British person wants to fix the units by Celsius and the metric system such as "m" and "m/s", the British person sets bit 1 of offset 4 to "1". Also, when any units of Celsius and the metric system such as "m" and "m/s" or Fahrenheit and the yard-pound system such as "Feet", "pound" and "yard" may be used, the British person sets bit 1 of offset 4 to "0".

Figure 6:
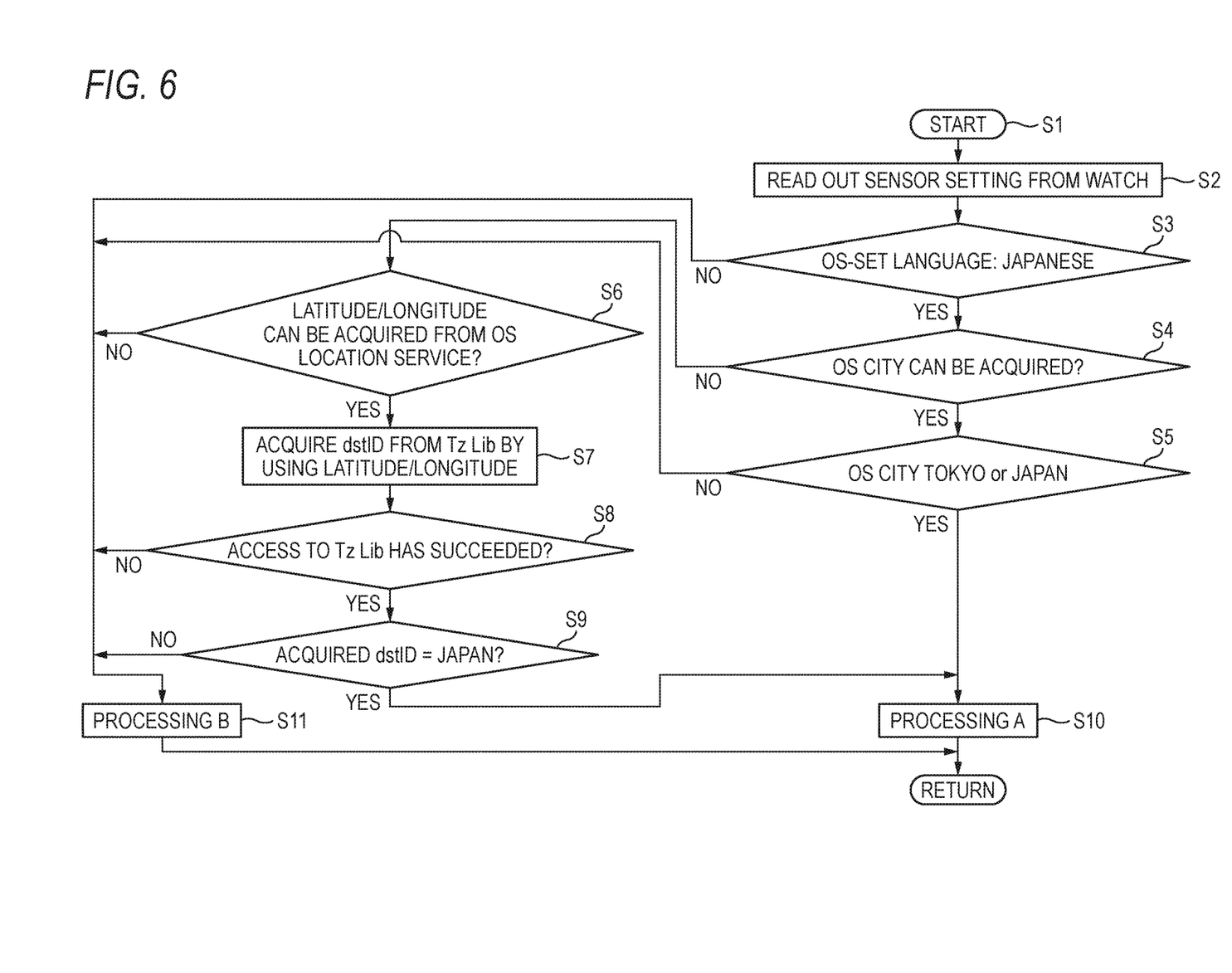
FIG. 6 is a flowchart (1) for illustrating a unit setting operation.

FIG. 6 is a flowchart (1) to illustrate a unit setting operation.

Routine of S1 is executed (i) when the electronic device 100 and the watch 200 are close to each other and can perform communication with each other, (ii) when a predetermined button (for example, a Bluetooth (registered trademark) button) of the electronic device 100 is pushed for time setting, or (iii) when time setting is executed periodically (for example, 4 times/day).

The electronic device-side control unit 10 first reads out the sensor setting 151 (FIG. 1) from the watch 200 (S2), and copies the sensor setting 151 to the sensor setting 51. After the copy, the electronic device-side control unit 10 determines whether an OS-set language is a language of the home time city 53, for example "Japanese" (S3). That is, the electronic device-side control unit 10 determines whether the display language (the OS-set display language 55 (FIG. 1)) set in the OS is Japanese. When it is determined that the OS-set language is Japanese (Yes in S3), the electronic device-side control unit 10 determines whether it is possible to acquire the OS city (the OS-set city 56 set in the OS) (S4). When it is determined that it is possible to acquire the OS city (Yes in 54), the electronic device-side control unit 10 proceeds to processing of 55, and determines whether the OS city (the OS-set city 56) is set as "TOKYO" or "JAPAN" (S5). Here, the setting as to whether the OS city is "TOKYO" or "JAPAN" depends on the specification of the OS. When it is determined that the OS city is set as "TOKYO" or "JAPAN" (Yes in S5), the electronic device-side control unit 10 executes processing A. That is, when the home time city 53, the region of the OS-set display language 55 and the OS-set city 56 are coincide with each other (are common), the electronic device-side control unit 10 executes processing A.

In the processing A, the electronic device-side control unit 10 sets bit 0 of offset 0 of the sensor setting 51 to "0", to set the altitude setting to "Meter". Also, the electronic device-side control unit 10 sets bit 0 of offset 1, to set the atmospheric pressure setting to "hPa". Also, the electronic device-side control unit 10 sets bit 0 of offset 2, to set the temperature setting to Celsius "°C.". Also, the electronic device-side control unit 10 sets bit 0 of offset 3 to "0", to set the GPS setting to "km". Also, the electronic device-side control unit 10 sets bit 0 of offset 4 to "1". That is, the electronic device-side control unit 10 fixes the display-units of the sensor setting 51 to "Meter", "hPa", "°C." and "km". Then, the electronic device-side control unit 10 transmits the changed sensor setting 51 to the watch 200 by using the electronic device-side communication unit 20 as a watch unit setting unit, and returns the processing to the original routine. Then, the watch-side control unit 110 writes the received setting to the sensor setting 151.

When it is determined in S3 that the OS-set language is not the language of the home time city 53, for example the OS-set language is not "Japanese" (No in S3), the electronic device-side control unit 10 executes processing B. In the processing B, the electronic device-side control unit 10 sets bit 0 of offset 4 to "0", to set that units may be displayed by Celsius "°C." and the metric system such as "m" and "m/s" or Fahrenheit "° F." and the yard-pound system such as "Feet", "yard" and "pound". That is, when the display-units of the sensor setting 51 are fixed to "Meter", "hPa", "°C." and "km", the setting is released.

When it is determined in S4 that it is not possible to acquire the OS-set city (No in S4), the electronic device-side control unit 10 determines whether it is possible to acquire latitude/longitude from the OS location service (S6). That is, the electronic device-side control unit 10 determines whether it is possible to acquire the latitude/longitude as the position information by using the position information acquisition unit 40. When it is determined that it is possible to acquire the latitude/longitude (Yes in S6), the electronic device-side control unit 10 acquires dstID (daylight saving time IDentification) from the Tz_Library 14 by using the acquired latitude/Longitude (S7). After the processing of S7, the electronic device-side control unit 10 determines whether the access to the Tz_Library 14 has succeeded (S8).

When it is determined that the access to the Tz_Library 14 has succeeded and it is possible to acquire the dstID (Yes in S8), the electronic device-side control unit 10 determines whether the dstID is "Japan", which is the home time city (S9). When it is determined that the dstID indicates Japan (Yes in S9), the electronic device-side control unit 10 executes the processing A (S10), and fixes the display-units of the sensor setting 51 to "Meter", "hPa", "°C." and "km". That is, when the home time city 53 and the OS city are coincided with the language region of the OS-set display language 55 or when the home time city 53 is included in the language region and the position information (latitude/longitude) is coincided with the home time city 53 or the language region, the electronic device-side control unit 10 executes the processing A to set the display-units to the units that are used in the corresponding city or region. On the other hand, when the home time city 53 is included in the region of the OS-set display language 55 even though the position information (latitude/longitude) does not correspond, the electronic device-side control unit 10 may execute the processing A.

When it is determined that it is not possible to acquire the latitude/longitude from the OS location service (No in S6), when it is determined that the access to the Tz_Library 14 has not succeeded (No in S7), or when the dstID does not indicate Japan (No in S9), the electronic device-side control unit 10 executes the processing B (S11) and releases the display-units of the sensor setting 51 set to "Meter", "hPa", "°C." and "km" if the display-units are fixed to the corresponding units. That is, even when any one of the home time city 53, the region of the OS-set display language 55 and the OS-set city 56 is not matched, the electronic device-side control unit 10 executes the processing B. Also, the display-units are set to the units that are used in the city or region in which the position information (latitude/longitude) and the home time city 53 or the region of the OS-set display language 55 are coincided with each other.

Second Embodiment

Figure 7:
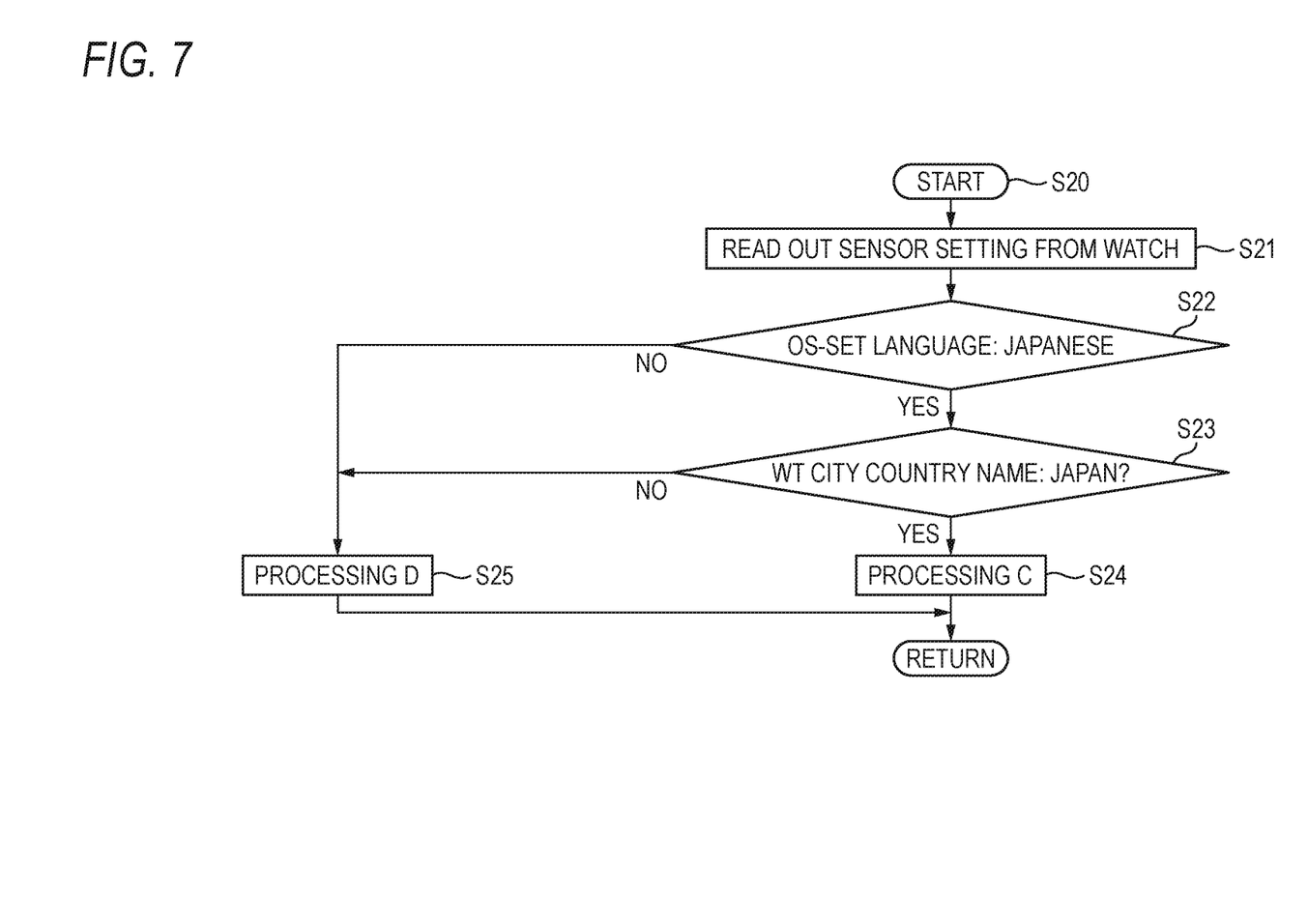
FIG. 7 is a flowchart (2) for illustrating a unit setting operation.

FIG. 7 is a flowchart (2) to illustrate a unit setting operation.

Routine of S20 is activated when the button to set the world time (WT) is pushed.

The electronic device-side control unit 10 first reads out the sensor setting 151 (FIG. 1) from the watch 200, and copies the sensor setting 151 to the sensor setting 51. After the copy, the electronic device-side control unit 10 determines whether the OS-set language is a language of the home time city 53, for example "Japanese" (S22). When it is determined that the OS-set language is Japanese (Yes in S22), the electronic device-side control unit 10 determines whether the world time city is Japan, which is a country name of the home time city (the home time city 53) (S23).

When it is determined that the world time city is Japan (Yes in S23), the electronic device-side control unit 10 executes processing C (S24), and returns to the original routine.

In the processing C, bit 1 of offset 4 of the sensor setting 51 copied in S21 is set to "1". Thereby, the units are fixed to the units ("Meter", "hPa", "°C." and "km") that are used in Japan, which is the world time city (WT 52).

On the other hand, when the OS-set language is not Japanese (No in S22) or when the world time city is not Japan, which is a country name of the home time city (No in S23), the electronic device-side control unit 10 executes processing D (S25), and returns to the original routine.

In the processing D, bit 1 of offset 4 of the sensor setting 51 copied in S21 is set to "0". Thereby, the units are set to the units ("Meter", "hPa", "°C." and "km") that are used in Japan, which is the world time city (WT 52), or to the other units ("Feet" "mmHg" "Mile", Fahrenheit).

By the above processing, even when the electronic device 100 and the watch 200 are separated from each other such that it is difficult to perform communication therebetween, the electronic device-side control unit 10 can store the setting (offset 4 of the sensor setting 51) as to whether the display-units are fixed to the units used in Japan or as to whether the display-units are set to the units in Japan or the other units.

For example, when a Japanese (the OS-set language: Japanese) resides in USA, the home time (HT) and the world time (WT) may be exchanged at the watch 200-side. Even in this case, the electronic device-side control unit 10 can store the setting corresponding to the world time city set at the electronic device 100-side.

Third Embodiment

Figure 8:
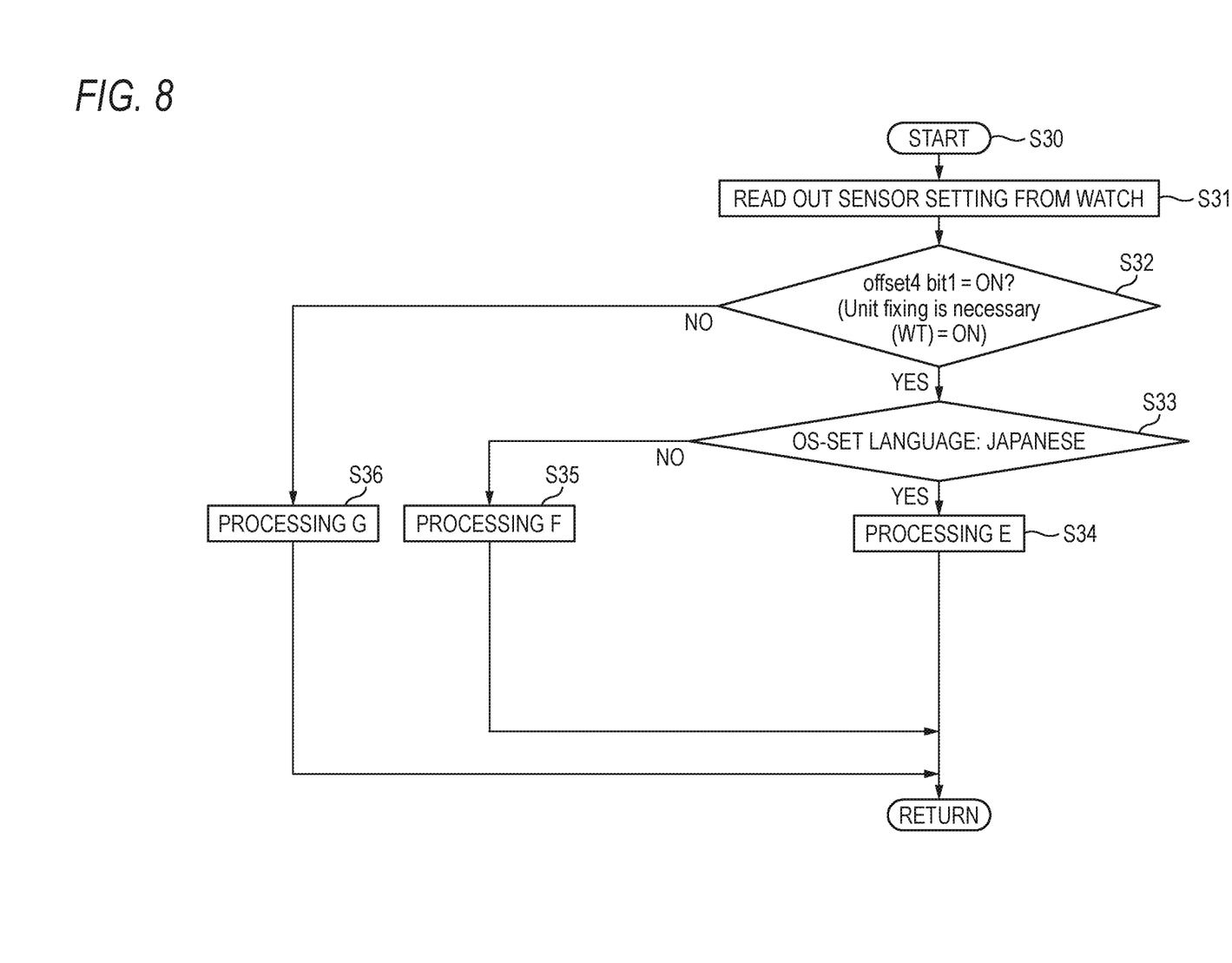
FIG. 8 is a flowchart (3) for illustrating a unit setting operation.

FIG. 8 is a flowchart (3) to illustrate a unit setting operation.

Routine of S30 is activated a button (HT/WT button) to exchange the home time (HT) and the world time (WT) at the electronic device 100-side is pushed.

The electronic device-side control unit 10 first reads out the sensor setting 151 (FIG. 1) from the watch 200 (S31), and copies the sensor setting 151 to the sensor setting 51. After the copy, the electronic device-side control unit 10 determines whether bit 1 of offset 4 has been set to "1" (S32). That is, the electronic device-side control unit 10 determines whether the display-units of the sensor settings 151, 51 read out in S31 are fixed to the region of the world time (WT).

When it is determined that the display-units are fixed to the region of the world time (WT) (Yes in S32), the electronic device-side control unit 10 determines whether the OS-set language is a language of the home time city 53, for example "Japanese" (S33). When it is determined that the OS-set language is Japanese (Yes in S33), the electronic device-side control unit 10 executes processing E (S34), and returns to the original routine. Then, the watch-side control unit 110 writes the received setting to the sensor setting 151.

In the processing E, the electronic device-side control unit 10 sets bit 0 of offset 0 of the sensor setting 51 to "0", to set the altitude setting to "Meter". Also, the electronic device-side control unit 10 sets bit 0 of offset 1 to "0", to set the atmospheric pressure setting to "hPa". Also, the electronic device-side control unit 10 sets bit 0 of offset 2 to "0", to set the temperature setting to Celsius "°C.". Also, the electronic device-side control unit 10 sets bit 0 of offset 3 to "0", to set the GPS setting to "km". That is, the electronic device-side control unit 10 fixes the display-units of the sensor setting 51 to "Meter", "hPa", "°C." and "km". Also, the electronic device-side control unit 10 executes processing of exchanging bit 0 and bit 1 of offset 4. By the exchanging of bits, the setting of the home time (HT) and the setting of the world time (WT) are exchanged.

On the other hand, when it is determined that the OS-set language is not Japanese (No in S33), the electronic device-side control unit 10 executes processing F (S35), and returns to the original routine. Then, the watch-side control unit 110 writes the received setting to the sensor setting 151.

In the processing F, the electronic device-side control unit 10 sets bit 0 of offset 4 to "0", thereby making a setting indicating that the display-units may be the display-units used in the home time city or may be the other display-units. That is, the electronic device-side control unit 10 makes a setting indicating that the display-units may be Celsius and the metric system of "m", "m/s" and the like or Fahrenheit and the yard-pound system of "Feet", "yard", "pound" and the like. In other words, the electronic device-side control unit 10 releases the state where the display-units are fixed to "Meter", "hPa", "°C." and "km". Also, the electronic device-side control unit 10 executes processing of exchanging bit 0 and bit 1 of offset 4.

Also, when it is determined that bit 1 of offset 4 is not set to "1" (No in S32), the electronic device-side control unit 10 executes processing G (S36), and returns to the original routine. Then, the watch-side control unit 110 writes the received setting to the sensor setting 151.

In the processing G, the electronic device-side control unit 10 changes bit 1 of offset 4 to "0", thereby making a setting indicating that the units may be the display-unit used in the world time city or the other display-units. That is, the electronic device-side control unit 10 releases the state where the display-units are fixed to "Meter", "hPa", "°C.," and "km". Also, the electronic device-side control unit 10 executes processing of exchanging bit 0 and bit 1 of offset 4.

By the above processing, the units that are to be displayed on the watch 200 are set to one of the state where the units are fixed and the state where the units can be appropriately changed. Whether the units to be displayed are to be fixed or not is automatically set by the display language that the user uses and the set city (region), so that it is possible to prevent the display-units from being unintentionally changed due to a user's operation and to optionally switch the display-units to be used by the user.

In the meantime, the present disclosure is not limited to the above embodiments, and can be changed without departing from the gist of the present disclosure. For example, the watch 200 may be an electronic terminal such as the other devices, an electronic calculator and a pedometer configured to display the units. The units to be displayed can also be appropriately changed.

What is claimed is:

1. An electronic device communicatively connected to an electronic terminal configured to display an output value of a sensor, the electronic device comprising:
    a storage unit that stores a first city to be set in the electronic terminal; and
    a processor,
    wherein the processor fixes or changes a display-unit of the output value of the sensor to be displayed on the electronic terminal, based on both the first city and a display language set in an OS of the electronic device,
    wherein the processor fixes the display-unit to a unit which is used in the first city when a language used in the first city is coincided with the display language, and
    wherein the processor sets the display-unit to be changeable to any unit when the language used in the first city is not coincided with the display language.

2. An electronic device communicatively connected to an electronic terminal configured to display an output value of a sensor, the electronic device comprising:
    a storage unit that stores a first city to be set in the electronic terminal; and
    a processor,
    wherein the processor fixes or changes a display-unit of the output value of the sensor to be displayed on the electronic terminal, based on both the first city and a display language set in an OS of the electronic device,
    wherein the processor determines whether the first city, a language region of the display language and an OS-set city set in the OS are coincided,
    wherein the processor fixes the display-unit to a unit that is used in the first city when the first city, the language region of the display language and the OS-set city set in the OS are coincided, and
    wherein the processor sets the display-unit to be changeable to any unit when any one of the first city, the language region of the display language and the OS-set city set in the OS is not coincided.

3. The electronic device according to claim 2, further comprising:
    a position information acquisition unit that acquires position information,
    wherein in a case where the first city is included in the language region of the display language, the processor determines whether the processor acquires the OS-set city based on the position information acquired by the position information acquisition unit,
    wherein when the processor acquires the OS-set city, the processor fixes the display-unit to a unit that is used in the acquired OS-set city, and
    wherein when the processor does not acquire the OS-set city, the processor sets the display-unit to be changeable to any unit.

4. The electronic device according to claim 1,
    wherein when communication with the electronic terminal starts, when a predetermined button is pushed or when the processor executes periodically, the processor sets or fixes the display-unit.

5. An electronic device communicatively connected to an electronic terminal configured to display an output value of a sensor, the electronic device comprising:
    a storage unit that stores a first city to be set in the electronic terminal and a second city to be set in the electronic terminal; and
    a processor,
    wherein the processor fixes or changes a display-unit of the output value of the sensor to be displayed on the electronic terminal, based on both the first city and a display language set in an OS of the electronic device,
    wherein in a case where a button to set the second city is pushed, when the set second city is coincided with a city in which the display language set in the OS is used, the processor fixes the display-unit to a unit that is used in the second city, and
    wherein when the set second city is not coincided with a city in which the display language set in the OS is used, the processor sets the display-unit to be changeable to any unit.

6. An electronic device communicatively connected to an electronic terminal configured to display an output value of a sensor, the electronic device comprising:
    a storage unit that stores a first city to be set in the electronic terminal;
    a processor,
        wherein the processor fixes or changes a display-unit of the output value of the sensor to be displayed on the electronic terminal, based on both the first city and a display language set in an OS of the electronic device; and a receiving unit that receives setting information indicating whether the display-unit is fixed to a unit that is used in a second city, wherein when the setting information indicates that the display-unit is fixed to the unit which is used in the second city and when the first city is included in a region of the display language set in the OS, the processor fixes the display-unit to a unit which is used in the first city, wherein when the setting information indicates that the display-unit is fixed to the unit which is used in the second city and the first city is not included in the region of the display language set in the OS, the processor releases a state where the display-unit is fixed to the unit which is used in the first city, and wherein when the setting information indicates that the display-unit is not fixed to the unit which is used in the second city, the processor releases the state where the display-unit is fixed to the unit which is used in the first city.

7. The electronic device according to claim 6,
wherein the processor exchanges the setting information indicating whether the display-unit is to be fixed to the unit which is used in the second city and setting information indicating whether the display-unit is to be fixed to the unit which is used in the first city.

8. The electronic device according to claim 6,
wherein the processor sets the display-unit when a button is pushed to exchange the first city and the second city.

9. The electronic device according to claim 1,
wherein the processor sets a display-unit of the electronic terminal.

10. A display-unit setting method of an electronic device communicatively connected to an electronic terminal configured to display an output value of a sensor, the display-unit setting method comprising:

storing a first city to be set in the electronic terminal; and fixing or changing a display-unit of the output value of the sensor to be displayed on the electronic terminal, based on both the first city and a display language set in an OS of the electronic device, wherein the display-unit is fixed to a unit which is used in the first city when a language used in the first city is coincided with the display language, and wherein the display-unit is set to be changeable to any unit when the language used in the first city is not coincided with the display language.

11. A non-transitory recording medium having a program to control a computer of an electronic device communicatively connected to an electronic terminal configured to display an output value of a sensor, the program causing the computer to function as:

storing a first city to be set in the electronic terminal; and fixing or changing a display-unit of the output value of the sensor to be displayed on the electronic terminal, based on both the first city and a display language set in an OS of the electronic device, wherein the display-unit is fixed to a unit which is used in the first city when a language used in the first city is coincided with the display language, and wherein the display-unit is set to be changeable to any unit when the language used in the first city is not coincided with the display language.

* * * * *